US00PP30247P3

(12) United States Plant Patent
Koekkoek

(10) Patent No.: US PP30,247 P3
(45) Date of Patent: Feb. 26, 2019

(54) CARNATION PLANT NAMED 'HILBECHCRA'

(50) Latin Name: *Dianthus caryophyllus*
Varietal Denomination: Hilbechcra

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 15/732,359

(22) Filed: Oct. 30, 2017

(65) Prior Publication Data

US 2018/0124978 P1 May 3, 2018

Related U.S. Application Data

(60) Provisional application No. 62/496,884, filed on Oct. 31, 2016.

(51) Int. Cl.
*A01H 5/02* (2018.01)
*A01H 6/30* (2018.01)

(52) U.S. Cl.
USPC ..... Plt./283
CPC ..... *A01H 5/02* (2013.01); *A01H 6/305* (2018.05)

(58) Field of Classification Search
USPC ..... Plt./272, 283
See application file for complete search history.

*Primary Examiner* — Susan McCormick Ewoldt
(74) *Attorney, Agent, or Firm* — C. A. Whealy

(57) ABSTRACT

A new and distinct cultivar of Carnation plant named 'Hilbechcra', characterized by its compact, uniformly mounding and upright to broadly spreading plant habit; relatively small leaves; freely flowering habit; red-colored double flowers; and good container and garden performance.

1 Drawing Sheet

Botanical designation: *Dianthus caryophyllus*.
Cultivar denomination: 'HILBECHCRA'.

BACKGROUND OF THE INVENTION

The present invention relates to a new and distinct cultivar of Carnation plant, botanically known as *Dianthus caryophyllus*, grown commercially as a container plant, previously known by the name 'Hilbchcrane' and hereinafter referred to by the name 'Hilbechcra'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in April, 2012 of a proprietary selection of *Dianthus caryophyllus* identified as code number A00001, not patented, as the female, or seed, parent with a proprietary selection of *Dianthus caryophyllus* identified as code number 1315, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2012.

Asexual reproduction of the new Carnation plant by terminal vegetative cuttings propagated in a controlled greenhouse environment in De Kwakel, The Netherlands since January, 2014 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbechcra'. These characteristics in combination distinguish 'Hilbechcra' as a new and distinct Carnation plant:

1. Compact, uniformly mounding and upright to broadly spreading plant habit.
2. Relatively small leaves.
3. Freely flowering habit.
4. Red-colored double flowers.
5. Good container and garden performance.

Plants of the new Carnation differ primarily from plants of the female parent selection in the following characteristics:

1. Plants of the new Carnation have longer branches than plants of the female parent selection.
2. Plants of the new Carnation are more freely branching than plants of the female parent selection.
3. Plants of the new Carnation flower about two weeks earlier than plants of the female parent selection.
4. Flowers of plants of the new Carnation are more fully double than flowers of plants of the female parent selection.

Plants of the new Carnation differ primarily from plants of the male parent selection in the following characteristics:

1. Plants of the new Carnation have larger flowers than plants of the male parent selection.
2. Flowers of plants of the new Carnation are more fully double than flowers of plants of the male parent selection.

Plants of the new Carnation also can be compared to plants of *Dianthus caryophyllus* 'Redcino', not patented. In side-by-side comparisons, plants of the new Carnation differ primarily from plants of 'Redcino' in the following characteristics:

1. Plants of the new Carnation have slightly broader leaves than plants of 'Redcino'.
2. Plants of the new Carnation have larger flowers than plants of 'Redcino'.
3. Flowers of plants of the new Carnation are more fully double than flowers of plants of 'Redcino'.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilbechcra' grown in a container.

DETAILED BOTANICAL DESCRIPTION

Plants used in the aforementioned photograph and following observations and measurements were grown during the summer in 10.5-cm containers in a glass-covered greenhouse in De Kwakel, The Netherlands and under cultural practices typical of commercial container Carnation production. During the production of the plants, day temperatures ranged from 16° C. to 23° C. and night temperatures ranged from 13° C. to 18° C. Plants used for the photograph and description were 13 weeks from planting and were pinched one time at the time of planting. In the following description, color references are made to The Royal Horticultural Society Colour Chart, 2015 Edition, except where general terms of ordinary dictionary significance are used.

Botanical classification: *Dianthus caryophyllus* 'Hilbechcra'.

Parentage:

*Female, or seed, parent*.—Proprietary selection of *Dianthus caryophyllus* identified as code number A00001, not patented.

*Male, or pollen, parent*.—Proprietary selection of *Dianthus caryophyllus* identified as code number 1315, not patented.

Propagation:

*Type*.—By terminal vegetative cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; moderately vigorous growth habit.

*Plant height, soil level to top of foliar plane*.—About 14 cm.

*Plant height, soil level to top of floral plane*.—About 14.3 cm.

*Plant diameter or spread*.—About 16.4 cm.

*Lateral branches*.—Branching habit: Freely branching habit with about five main (basal) stems; each main stem with about four lateral branches; pinching enhances lateral branch development. Length: About 11 cm. Diameter: About 4 mm. Internode length: About 1 cm. Strength: Strong. Aspect: Upright to about 30° from vertical. Texture and luster: Smooth, glabrous, waxy cuticle; matte. Color, developing: Close to 145C; at internodes, close to 145A. Color, developed: Close to 145A; thin waxy cuticle, close to 193A to 193B.

Leaf description:

*Arrangement*.—Opposite, simple; sessile.

*Length*.—About 8.9 cm.

*Width*.—About 7.5 mm.

*Shape*.—Narrowly oblanceolate; moderately to strongly curled.

*Apex*.—Acute.

*Base*.—Attenuate; decurrent.

*Margin*.—Entire.

*Texture and luster, upper and lower surfaces*.—Smooth, glabrous, waxy cuticle; slightly glossy.

*Venation pattern*.—Parallel.

*Color*.—Developing leaves, upper surface: Close to 137C to 137D. Developing leaves, lower surface: Close to 138B. Fully expanded leaves, upper surface: Close to between NN137A and 147A; venation, close to NN137B; thin waxy cuticle, close to 189A. Fully expanded leaves, lower surface: Close to NN137B; venation, close to 144A; thin waxy cuticle, close to 189A to 189B.

Flower description:

*Flower form and flowering habit*.—Double type flowers arranged singly or in pairs; freely flowering habit with about 19 flowers per plant at one time; flowers face mostly upright to slightly outwardly.

*Natural flowering season*.—Flowering is continuous from the spring to late summer in The Netherlands; plants begin flowering about 13 weeks after planting.

*Postproduction longevity*.—Flowers last about ten days on the plant; flowers not persistent.

*Fragrance*.—Moderately fragrant; clove-like, sweet and pleasant.

*Flower buds*.—Length: About 2 cm. Diameter: About 1.3 cm. Shape: Obovate. Texture and luster: Smooth, glabrous; matte. Color: Close to 143C; towards the base, close to 144B to 144C; petal apices, tinged with close to 35A to 35B.

*Flower diameter*.—About 5.9 cm.

*Flower depth*.—About 4.5 cm.

*Petals*.—Quantity and arrangement: About five petals arranged in a single whorl. Length: About 4.2 cm. Width: About 2.4 cm. Shape: Spatulate. Apex: Irregularly dentate and praemorse. Base: Narrowly cuneate. Margin: Irregularly dentate; undulate. Texture and luster, upper surface: Smooth, glabrous; velvety; matte. Texture and luster, lower surface: Smooth, glabrous; slightly velvety; matte. Color: When opening, upper surface: Close to 46D; at the base, close to 145C. When opening, lower surface:

Close to 47C to 47D; at the base, close to 145C. Fully opened, upper surface: Close to 46C; at the base, close to 145C; venation, similar to lamina colors; colors do not change with development. Fully opened, lower surface: Close to 45C; at the base, close to 145C; venation, similar to lamina colors; colors do not change with development.

*Petaloids*.—Quantity and arrangement: About 75 petaloids arranged in about ten whorls. Length: About 3 cm to 4.1 cm. Width: About 0.7 cm to 2.3 cm. Shape: Spatulate. Apex: Irregularly dentate and praemorse. Base: Narrowly cuneate. Margin: Irregularly dentate; undulate. Texture and luster, upper surface: Smooth, glabrous; velvety; matte. Texture and luster, lower surface: Smooth, glabrous; slightly velvety; matte. Color: When opening, upper surface: Close to 46D; at the base, close to 145C. When opening, lower surface: Close to 47C to 47D; at the base, close to 145C. Fully opened, upper surface: Close to 46C; at the base, close to 145C; venation, similar to lamina colors; colors do not change with development. Fully opened, lower surface: Close to 45C; at the base, close to 145C; venation, similar to lamina colors; colors do not change with development.

*Sepals*.—Quantity and arrangement: Five sepals arranged in a single whorl; proximal 75% portion of the sepals are fused into a campanulate-shaped calyx. Calyx length: About 2.4 cm. Calyx diameter: About 1.5 cm. Sepal length: About 2.7 cm. Sepal width, at base of "free" portion: About 1 cm. Shape: Obovate. Apex: Acute. Margin: Entire. Texture and luster, upper surface: Smooth, glabrous; glossy. Texture and luster, lower surface: Smooth, glabrous; matte. Color: When opening, upper surface: Close to 191A; at the apex, close to 144C. When opening, lower surface: Close to 143C; towards the base, close to 144B to 144C; apex, tinged with close to 35A to 35B. Fully opened, upper surface: Close to 191A; at the apex, close to 144C to 144D. Fully opened, lower surface: Close to 143A; towards the base, close to 144C.

*Peduncles*.—Length: About 5 mm. Diameter: About 3 mm. Strength: Moderately strong. Aspect: About 35° from the stem axis. Texture and luster: Smooth, glabrous, waxy; matte. Color: Close to NN137D; thin waxy layer, close to 190A to 190B.

*Reproductive organs*.—Stamens: Quantity: About 30 stamens per flower; significantly deformed. Filament length: About 0.5 cm to 1.1 cm. Filament color: Close to NN155D. Anther size: About 1 mm by 0.5 mm. Anther shape: Irregularly oblong, deformed. Anther color: Close to 165C to 165D. Pollen: None observed to date. Pistils: Quantity: About two per flower. Pistil length: About 2.8 cm. Stigma diameter: About 3 mm. Stigma shape: Pointed, curved. Stigma color: Close to 61D. Style length: About 2.6 cm. Style color: Close to 61D; towards the base, close to NN155D. Ovary color: Close to N144D. Fruits and seeds: Fruit and seed development have not been observed on plants of the new Carnation to date.

Disease & pest resistance: Plants of the new Carnation have not been observed to be resistant to pathogens and pests common to Carnation plants to date.

Garden performance: Plants of the new Carnation have been observed to tolerate rain, wind, high temperatures about 35° C. and to be suitable for USDA Hardiness Zones 5 to 9.

It is claimed:

1. A new and distinct Carnation plant named 'Hilbechcra' as illustrated and described.

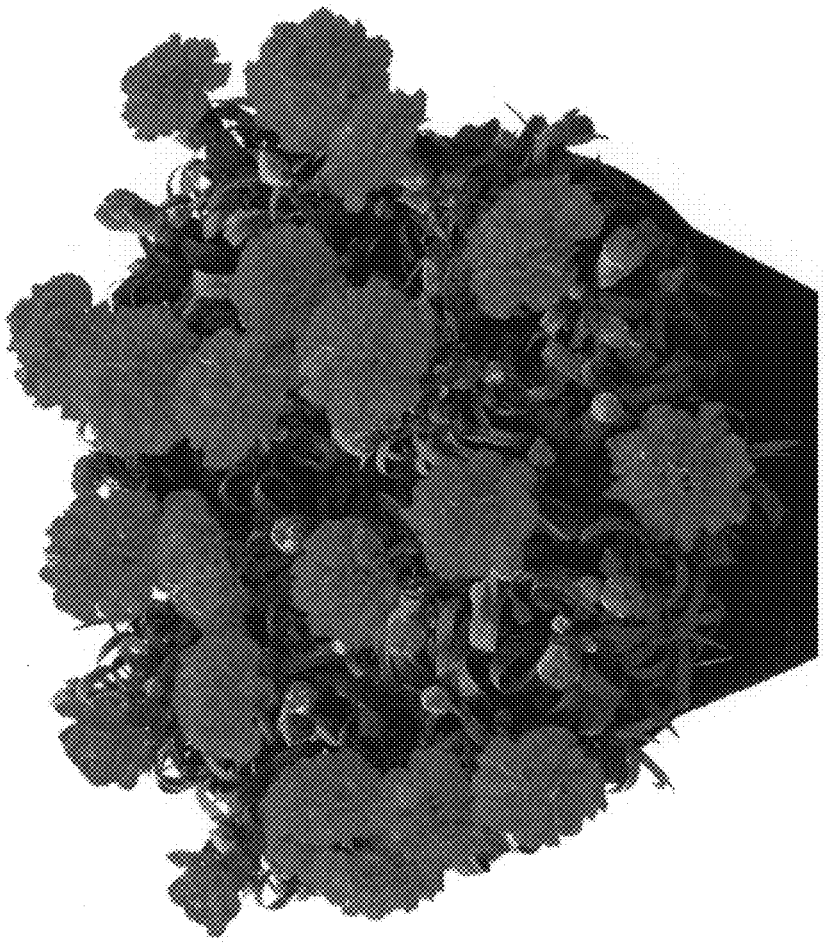

* * * * *